United States Patent [19]

Oien

[11] 4,310,308

[45] Jan. 12, 1982

[54] DUAL-SIDE ASPIRATOR FOR DENTAL DAM

[75] Inventor: Hal J. Oien, Portland, Oreg.

[73] Assignee: Jordco, Inc., Portland, Oreg.

[21] Appl. No.: 176,051

[22] Filed: Aug. 7, 1980

Related U.S. Application Data

[63] Continuation of Ser. No. 44,244, May 31, 1979, abandoned.

[51] Int. Cl.³ .............................................. A61C 17/04
[52] U.S. Cl. ...................................... 433/91; 433/136
[58] Field of Search ....................... 433/91, 92, 93, 94, 433/95, 96, 136, 137, 138, 139, 140; 128/276

[56] References Cited

U.S. PATENT DOCUMENTS

| 175,706 | 4/1876 | Howells | 433/136 |
| 602,572 | 4/1898 | Browne et al. | 433/92 |
| 1,930,196 | 10/1933 | Fisher | 433/94 |
| 1,986,751 | 1/1935 | Robinson | 433/91 |
| 3,027,643 | 4/1962 | Cohen | 433/94 |
| 3,090,122 | 5/1963 | Erickson | 433/93 |
| 3,396,468 | 8/1968 | Dayhoff | 433/93 |
| 3,426,430 | 2/1969 | Newman | 433/96 |
| 3,965,901 | 6/1976 | Penny et al. | 128/276 |
| 4,240,789 | 12/1980 | Rosenthaler | 433/91 |

Primary Examiner—Gene Mancene
Assistant Examiner—John J. Wilson
Attorney, Agent, or Firm—Kolisch, Hartwell & Dickinson

[57] ABSTRACT

Apparatus for aspirating liquids and debris which collect near the working region of a dental dam. The apparatus includes a head adapted to extend removably and sealingly through a stretched aperture in such a dam, with the head having aspirating ports that open on opposite surfaces of the dam. These ports couple with an exhaust passage, which extends on the nonworking side of the dam, and which is adapted for coupling to a flexible suction conduit.

4 Claims, 5 Drawing Figures

DUAL-SIDE ASPIRATOR FOR DENTAL DAM

CROSS-REFERENCE TO RELATED APPLICATION

This application is a continuation of my prior-filed copending application Ser. No. 44,244, entitled "Dual Dental Rubber Dam Aspirator", filed May 31, 1979, and now abandoned.

BACKGROUND AND SUMMARY OF THE INVENTION

This invention pertains to dental apparatus, and more particularly to a device for aspirating opposite sides of a dental dam during a dental procedure. Many dentists use what is known as a dental dam to isolate the place in a person's mouth where they plan to perform some procedure. The typical dam takes the form of a thin pliable membrane which is perforated to fit over one or more teeth, and which is held in place by a suitable clamp, or the like. The dam exposes, and isolates, the desired working area, and at the same time protects other areas in the mouth. It is usual that, during use of a dam, fluids and debris will collect in the mouth on opposite sides of the dam.

A general object of the present invention is to provide an extremely simple and effective device usable with such a dam to aspirate such fluids and debris from opposite sides of the dam during a dental procedure.

According to a preferred embodiment of the invention, the apparatus thereof includes an aspirating head adapted to be fitted snugly and sealingly in a suitable aperture prepared in a dam, with this head having ports or openings which open to opposite sides of the dam, and which communicate with a common exhaust passage. A flexible hose connects with the head to apply suction to the latter-mentioned passage.

With the aspirating head in place relative to a dam during a particular procedure, continual convenient aspiration is provided on opposite sides of the dam in the region immediately adjacent the working area. This situation affords a great deal of convenience for the dentist, as well as comfort for the patient.

These and other objects and advantages which are attained by the invention will become more fully apparent as the description which now follows is read in conjunction with the accompanying drawings, wherein.

Figure 1:
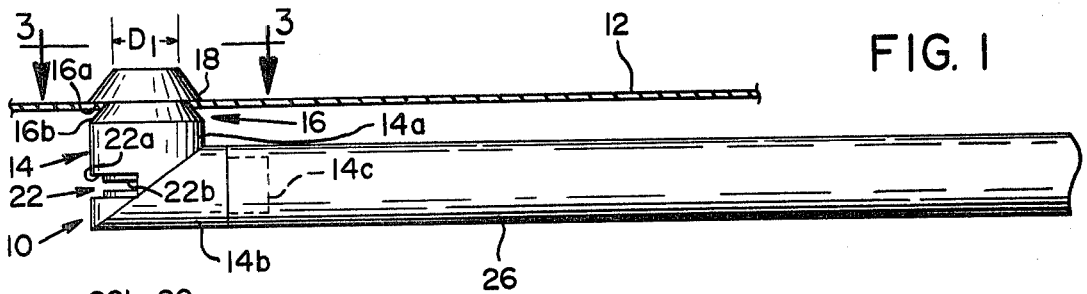
FIG. 1 is a side elevation, on a larger than true life size illustrating aspiration apparatus constructed in accordance with the invention connected for use with a dental dam which is shown outside of the environment of a person's mouth.
Figure 2:
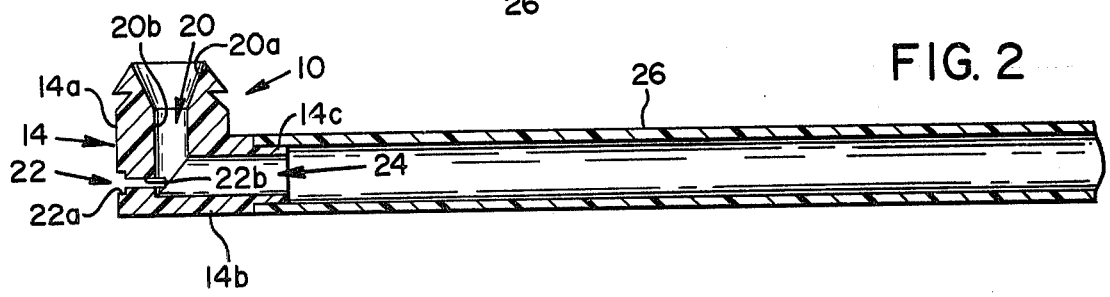
FIG. 2 is somewhat like FIG. 1, except that it illustrates a vertical section through the apparatus of FIG. 1, and with the further exception that the dam of FIG. 1 is removed in FIG. 2.
Figure 3:
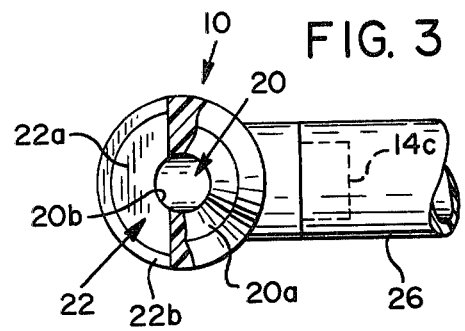
FIG. 3 is a fragmentary view taken generally along the line 3—3 in FIG. 1, on a larger scale than FIG. 1, with the dam of FIG. 1 removed, and with portions broken away to illustrate details of construction.
Figure 5:
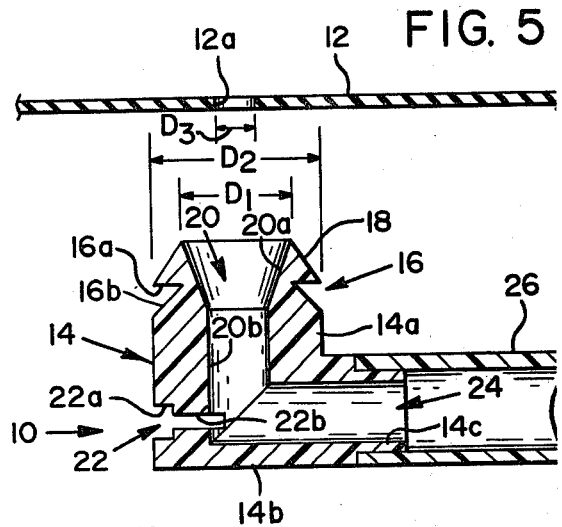
Figure 4:
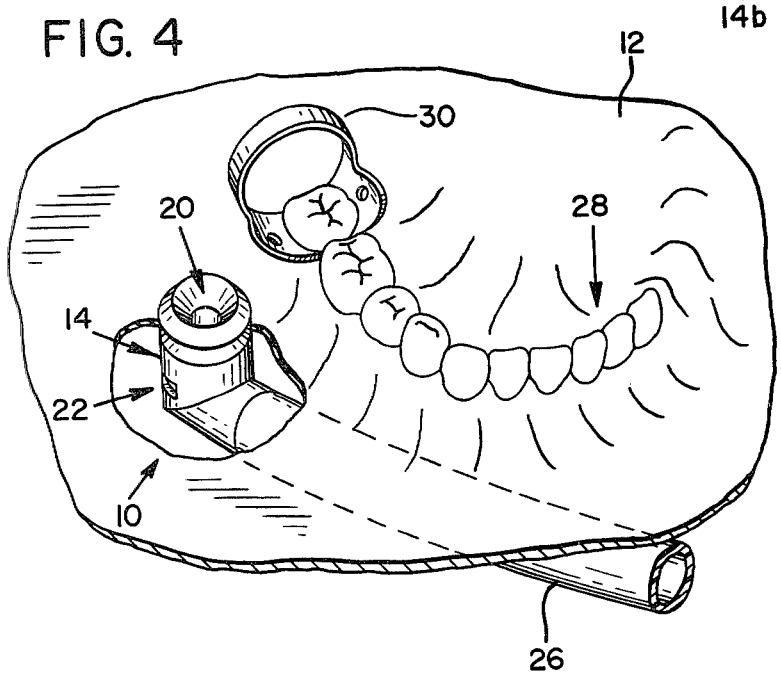

FIG. 4 is on a smaller scale than FIGS. 1, 2 and 3, and illustrates the apparatus of the invention connected to a dam which is shown (fragmentarily) within the environment of the lower portion of a person's mouth; and FIG. 5 is a view, on the largest scale used in the drawings, illustrating certain dimensions in the apparatus of the invention as compared to those of an aperture which has been prepared in a dam to receive the apparatus.

DETAILED DESCRIPTION OF THE INVENTION

Turning now to the drawings, and referring first to FIGS. 1-3, inclusive, indicated generally at 10 is aspirating apparatus constructed according to the invention, which apparatus, in FIG. 1, is shown connected in an operative condition with a conventional rubber dental dam 12. Apparatus 10 includes an aspirating head 14 formed with two right-angularly intersecting cylindrical portions 14a, 14b. Head 14 herein is a unitary structure molded of a suitable rigid plastic material.

Extending circumferentially about the upper part of head portion 14a is a groove 16 defined by an upper planar shoulder 16a and a lower beveled shoulder 16b. Where these two shoulders meet at an acute angle, they define what is referred to herein as the base diameter for the groove, which diameter is indicated in FIG. 1 at $D_1$. Formed in head portion 14a, immediately above groove 16, is a taper or overbevel 18.

Extending axially into portion 14a, and opening at the top of head 14 is a passage, or port, 20 having, as can be seen in FIGS. 2 and 3, a truncated conical upper portion 20a which joins with a cylindrical lower portion 20b. This passage is referred to herein as a first aspirating passage.

Near the base of head 14 is another passage, or port, 22 which is referred to as a second aspirating passage. Passage 22 extends in a plane substantially normal to the axis of head portion 14a, with a semicircular configuration (see FIG. 3) which occupies nearly one-half the cross-sectional area of head 14. Passage 22 includes an outer semiannular portion 22a having one vertical height in FIGS. 1 and 2, which outer portion joins with an inner generally semicircular portion 22b whose vertical height is less than that of portion 22a.

Extending in head portion 14b, substantially at a right angle to the axis of passage 20, is yet a third passage 24 (see FIG. 2) which is referred to herein as an exhaust passage. Exhaust passage 24 communicates, as can be seen in FIG. 2, both with passage 20 and with passage 22.

Completing a description of what is shown in FIGS. 1-3, inclusive, head portion 14b, adjacent its right end in the figures, includes a reduced-diameter section 14c which receives one end of a flexible hose 26. The other end of hose 26 (not shown) is connected in the usual manner to a conventional dental suction apparatus.

Turning to FIG. 5, apparatus 10 and dam 12 are shown herein in a condition just prior to their being connected. Here, certain important dimensional relationships are clearly illustrated. Previously mentioned dimension $D_1$ is the base diameter of groove 16. Indicated at $D_2$ is the outside diameter of head portion 14a. Indicated at $D_3$ is the relaxed-state diameter of an aperture 12a which has been prepared in dam 12 to receive head 14.

It will be noted that diameter $D_3$ is considerably smaller than diameter $D_1$. Thus, the dam is prepared for receiving head 14 with a relaxed-state aperture which is considerably smaller than the base diameter of groove 16. The purpose of this dimensional difference is to assure a tight fluid-sealing fit between the dam and head 14 when the two are connected.

To make such a connection, the dam, in the region of aperture 12a, is stretched to fit over the upper end of head portion 12a, with taper 18 serving like a cam to guide the aperture toward groove 16. With groove 16 fully receiving the aperture, beveled shoulder 16b, cooperating with tension developed in the circumference of aperture 12a, tends to urge the dam into a tightly sealed coplanar relationship with planar shoulder 16a.

Explaining now how apparatus 10 performs with dam 12, FIG. 4 shows the two in place in a person's mouth during a typical dental procedure. Indicated generally at 28 in FIG. 4 is a partial row of teeth in a person's lower jaw, which teeth are intended to be exposed during the procedure. Accordingly, suitable apertures for receiving these teeth have been prepared in the usual manner in dam 12, with the same then fitted over the exposed teeth, and retained by a conventional clamp shown at 30. The upper surface of dam 12—the one which is exposed to the viewer in FIG. 4—is referred to herein as the working-side surface of the dam. The nonexposed undersurface of the dam is referred to herein as the nonworking-side surface of the dam.

During the procedure, fluids and debris collect on opposite sides of the dam in the region of the working area, with most of the debris, of course, confined to the working-side surface of the dam.

With apparatus 10 connected to the dam as shown, so as to place head 14 in a position closely adjacent the working area, and with suction applied to the apparatus through hose 26 (in a conventional manner), passage 20 conveniently aspirates unwanted material from the working-side surface of the dam, while passage 22 performs the same function on the nonworking-side surface of the dam. Since it is expected that more materials which are to be aspirated will collect on the working-side surface of the dam, vis-a-vis that which is expected to collect on the nonworking-side surface of the dam, passage 20a has a considerably larger cross-sectional area than passage 22. Passage 22 functions, primarily, to aspirate saliva. It is given the shape illustrated in order to minimize the chance of its becoming blocked by adjacent mouth tissue.

It should thus be apparent how the apparatus of the invention offers a simple and convenient method for aspirating opposite sides of a dental dam. Its placement relative to the working area defined by a dam is completely at the discretion of the dentist in his preparation of a receiving aperture in the dam. Effective aspiration takes place simultaneously on both sides of the dam, immediately in the area of the dental procedure.

The head in apparatus 10 is quickly and easily fitted with a dam, and after a dental procedure, is easily disconnected, either for sterilization and reuse, or for discarding.

While no exact dimensions have been given herein, these are considered to be a matter of choice, recognizing that it is desirable to maintain the overall bulk of the apparatus as small as possible for the sake of patient comfort. While rigid plastic has been specified as a desirable material for making apparatus 10, other relatively rigid materials may, of course, be used.

Therefore, while a preferred embodiment of the invention has been shown and described herein, it is appreciated that variations and modifications may be made without departing from the spirit of the invention.

It is claimed and desired to secure by Letters Patent:

1. Aspirating apparatus in combination with a dental dam of the type including opposed surfaces, one of which forms a working-side surface, and the other of which forms a nonworking-side surface, and a generally circular aperture with a defined relaxed-state diameter extending between and opening to such surfaces, said apparatus, in operative condition with respect to such a dam, comprising an aspirating head including one portion having a generally cylindrical configuration formed with a reduced-diameter, outwardly facing, substantially circular groove with a base diameter exceeding the relaxed-state diameter of the aperture in the dam sealingly and removably receiving the circumferential margin of the aperture, with such margin, as so received, in a tensed and stretched state, means in said head defining a first aspirating passage exposed on the working-side surface of the dam, means in said head defining a second aspirating passage exposed on the nonworking-side surface of the dam, and means in said head defining an exhaust passage arranged in fluid communication with said first and second aspirating passages, and extending on the nonworking-side surface of the dam.

2. The apparatus of claim 1, wherein said head includes another portion extending generally radially relative to the axis of said one portion formed to accommodate the coupling of an external conduit in fluid communication with said exhaust passage.

3. The apparatus of claim 1, wherein said groove includes a substantially planar annular shoulder disposed in substantial coplanar contact with the working-side surface margin of the aperture in the dam.

4. The apparatus of claim 3, wherein said groove further includes a beveled shoulder extending at an outwardly facing acute angle relative to said first-mentioned shoulder acting on the nonworking-side surface margin of the aperture in the dam and tending to urge the margin of the aperture toward the first-mentioned shoulder.

* * * * *